(12) United States Patent
Lawlor

(10) Patent No.: US 6,685,921 B2
(45) Date of Patent: Feb. 3, 2004

(54) DENTAL CARE COMPOSITIONS

(75) Inventor: Thomas Mark Lawlor, Ashford (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/424,640

(22) Filed: Apr. 25, 2003

(65) Prior Publication Data

US 2003/0198604 A1 Oct. 23, 2003

Related U.S. Application Data

(63) Continuation of application No. PCT/US00/29384, filed on Oct. 25, 2000.

(51) Int. Cl.$^7$ ............... A61K 7/16; A61K 7/48; C08L 83/04; C09K 3/00; A61C 5/00

(52) U.S. Cl. ............. 424/49; 433/228.1; 523/116; 523/118

(58) Field of Search ............ 424/49–58; 523/116, 523/118; 433/228.1

(56) References Cited

U.S. PATENT DOCUMENTS

| | | |
|---|---|---|
| 2,736,721 A | 2/1956 | Dexter et al. |
| 2,814,601 A | 11/1957 | Currie et al. |
| 3,929,704 A | 12/1975 | Horning |
| 3,956,480 A | 5/1976 | Dichter et al. |
| 4,016,328 A | 4/1977 | Horning |
| 4,161,518 A | 7/1979 | Wen et al. |
| 4,902,499 A | 2/1990 | Bolish, Jr. et al. |
| 4,906,459 A | 3/1990 | Cobb et al. |
| 5,032,387 A | 7/1991 | Hill et al. |
| 5,057,307 A | 10/1991 | Hill et al. |
| 5,057,309 A | 10/1991 | Hill et al. |
| 5,139,768 A | 8/1992 | Friedman |
| 5,401,528 A | 3/1995 | Schmidt |
| 5,422,098 A | 6/1995 | Rolla et al. |
| 5,425,953 A | 6/1995 | Sintov et al. |
| 5,438,076 A | 8/1995 | Friedman et al. |
| 5,523,017 A | 6/1996 | Moran et al. |
| 5,733,529 A | 3/1998 | Hill et al. |
| 5,888,491 A | 3/1999 | Mitra et al. |
| 5,939,052 A | 8/1999 | White, Jr. et al. |
| 5,958,448 A * | 9/1999 | Ekeland et al. ............. 424/450 |
| 5,989,535 A | 11/1999 | Nayak |
| 6,017,546 A * | 1/2000 | Glover ............. 424/401 |
| 6,187,295 B1 | 2/2001 | Glandorf |
| 6,190,644 B1 | 2/2001 | McClanahan et al. |
| 6,350,436 B1 | 2/2002 | Glandorf et al. |
| 6,451,295 B1 * | 9/2002 | Cai et al. ............. 424/400 |
| 6,521,216 B1 | 2/2003 | Glandorf et al. |
| 6,555,094 B1 | 4/2003 | Glandorf et al. |
| 6,569,408 B1 * | 5/2003 | Yue et al. ............. 424/49 |
| 6,589,512 B1 * | 7/2003 | Yue et al. ............. 424/49 |

FOREIGN PATENT DOCUMENTS

| | | |
|---|---|---|
| CA | 2085696 | 12/1992 |
| EP | 0528457 B1 | 2/1993 |
| EP | 0 736544 B1 | 9/1996 |
| EP | 0822233 A2 | 2/1998 |
| EP | 0 8643515 A3 | 9/1998 |
| EP | 1027877 A1 | 8/2000 |
| GB | 686429 | 1/1953 |
| GB | 789851 | 1/1958 |
| GB | 2289686 A | 11/1995 |
| WO | WO 92/08439 A1 | 5/1992 |
| WO | WO 92/10161 A1 | 6/1992 |
| WO | WO 92/10162 A1 | 6/1992 |
| WO | WO 93/14737 A1 | 8/1993 |
| WO | WO 93/17660 A1 | 9/1993 |
| WO | WO 93/23009 A1 | 11/1993 |
| WO | WO 93/24103 A1 | 12/1993 |
| WO | WO 95/03776 A1 | 2/1995 |
| WO | WO 96/19190 A1 | 6/1996 |
| WO | WO 96/19191 A1 | 6/1996 |
| WO | WO 96/19192 A1 | 6/1996 |
| WO | WO 96/19563 A1 | 6/1996 |
| WO | WO 97/17058 A1 | 5/1997 |
| WO | WO 97/17059 A1 | 5/1997 |
| WO | WO 97/25968 A1 | 7/1997 |
| WO | WO 98/16196 A1 | 4/1998 |
| WO | WO 00/06100 A1 | 2/2000 |
| WO | WO 00/06107 A1 | 2/2000 |
| WO | WO 01/01939 A1 | 1/2001 |
| WO | WO 01/01940 A1 | 1/2001 |
| WO | 20023421 * | 5/2002 |

* cited by examiner

*Primary Examiner*—Shep K. Rose
(74) *Attorney, Agent, or Firm*—Emelyn L. Hiland

(57) ABSTRACT

Disclosed are non volatile oral care compositions that comprise:

i) from about 0.5% to about 60%, by weight, of a silicone resin;

ii) from about 0.1% to about 30%, by weight, of a silicone gum;

iii) from about 0.1% to about 95%, by weight, of a non volatile polysiloxane fluid which has a viscosity from about 1 cStk to about 1000 cStk; and iv) from about 0.01% to about 50%, by weight, of an oral care active selected from teeth color modifying substances, anti-tartar agents, anti-plaque agents, fluoride ion sources, anti-microbial agents, nutrients, antioxidants, H-2 antagonists, analgesics, anti-viral agents, mucosally absorbed pharmacological agents and mixtures thereof.

A second aspect of the present invention relates to the use of non volatile oral care silicone compositions in the oral cavity to treat the hard and soft tissue surfaces wherein the composition comprises:

(i) from about 0.5% to about 60%, by weight, of a silicone resin;

(ii) from about 0.1% to about 30%, by weight of a silicone gum;

(iii) from about 0.1% to about 95%, by weight, of a non volatile polysiloxane fluid which has a viscosity from about 1 cStk to about 1000 cStk.

Compositions of the present invention are useful for providing a substantive composition on the surfaces of the oral cavity which can provide prophylactic, therapeutic or cosmetic benefits.

17 Claims, No Drawings

DENTAL CARE COMPOSITIONS

CROSS REFERENCE TO RELATED APPLICATION

This application is a continuation of International Application PCT/US00/29384 with an international filing date of Oct. 25, 2000.

FIELD OF THE INVENTION

The present invention relates to oral care compositions, which comprise a silicone resin, a silicone gum and a silicone fluid, and to the use of such oral care compositions to treat the hard and soft tissue surfaces of the oral cavity. More particularly, this invention relates to silicone oral care compositions which form a substantive film on the surface of the teeth or gums treating these surfaces and which are readily removed by brushing, rinsing or eating at the end of the treatment period. According to one aspect of this invention the compositions can also comprise an oral care active and as such can provide sustained delivery of this active to the tissues of the oral cavity. Compositions of the present invention are particularly useful for delivering of oral care actives, which either enhance the appearance of the teeth or provide therapeutic and/or prophylactic benefits.

BACKGROUND

Many consumers have a good understanding of the prophylactic, therapeutic and cosmetic benefits of maintaining high standards in oral hygiene. These benefits include reduction in caries, plaque, gingivitis and tartar; treating hypersensitivity; freshening breath; whitening teeth and removing stains; remineralising teeth and the like. To date, a wide variety of oral care products are available which, over the short term, aid the maintenance of good oral hygiene by delivering various oral care substances or actives to the soft and hard tissues of the oral cavity. In general such products exist in the form that they are used by the consumer themselves either at-home or away from the home and/or are administered by dentists/hygienists as part of their professional routine of oral hygiene treatments. Specific examples of such products, particularly those for use by the consumer themselves, include dentifrices containing for example anti-caries actives and/or anti-bacterial plaque reducing actives; mouth washes containing breath freshening actives and/or anti-bacterial actives; and chewing gums containing tooth whitening actives.

The most frequently used oral hygiene treatments are those administered by the consumer themselves and it is usual that these are practised, in the Western world, either once or twice a day. However, many of the processes which lead to a deterioration in the tissues of the oral cavity are on-going and, as such, can only be effectively treated, either prophylactically or therapeutically, by continuous attention which is impractical or by the use of long lasting treatments. To date, conventional product forms do not typically provide long lasting, prolonged or sustained therapeutic, prophylactic and/or cosmetic treatment benefits. Instead the preparations take effect only for the relatively short period of time during which the teeth are being cleaned or the mouth is being rinsed and, after product use, the active level on the hard and soft oral tissues diminishes rapidly. Thus, until now, the only way to achieve sustained active release with conventional products has been to periodically reapply the product or to use a special delivery device or containment means such as a mouthpiece. It would therefore be desirable to have an oral care product comprising one or more active substances which is itself substantive within the oral cavity and wherein the oral care product has a pleasant mouth feel such that its aesthetics are acceptable for long term use in the oral cavity. It is also desirable to have a substantive oral care product wherein the active substances are released over a sustained period of time and thus able to provide a long lasting benefit. Finally it would be desirable if this oral care product was easily removed at the end of the treatment period such that no damage is sustained to the hard or soft tissues of the oral cavity in removing the product and such that the oral care product is suitable for home use by the consumer without the need for professional assistance. Furthermore such compositions would be especially useful in the many less well developed areas of the world where prophylactic professional dental hygiene is less commonly available.

Several attempts have previously been made to enhance the substantivity of active components of oral care products within the oral cavity. These attempts include the use of film forming polymers to deliver various actives for example bleaching agent (U.S. Pat. No. 5,425,953, International Patent Appln. No. PCT/CN97/00004 published on Jul. 24, 1997 as WO 97/25968); bactericidal pharmacological agent (U.S. Pat. No. 5,438,076); anti-plaque cationic bactericide (EP 0,864,315); fluoride ions (U.S. Pat. No. 5,989,535) etc. However, because some of the above systems are water soluble they readily dissolve in saliva and therefore their degree of durability is relatively low and they can not provide long term delivery of the active ingredient. In addition, their water soluble nature precludes them from being used in conjunction with oral care actives that would be unstable in water based films, for example sodium percarbonate. A second strategy that has been disclosed in the art for the improvement of the substantivity of actives within the oral cavity is the use of materials which are able to adsorb to the tissue. For example U.S. Pat. No. 3,956,480 discloses compositions in which cationic germicide and anionic polymer are adsorbed onto the hydroxyapatite surface of the teeth; EP0736544 discloses the use of antibodies to adhere to specific proteins in the oral cavity for example in the pellicle structures; EP 1,027,877 and U.S. Pat. No. 5,139,768 disclose compositions comprising hydrophobic polymers for example cellulosic or carbonyloxycarbonyl polymers to achieve substantivity; and WO 93/24103 discloses an antimicrobial agent supported on an inert oxide synthetic particulate which adsorbs onto the tooth enamel. However, these methods are limited in that the materials tend to have a preferred affinity for the hard tissues of the oral cavity and furthermore they can be limited in the type of oral care actives that can be incorporated. Higher degrees of durability have been achieved by the use of hard protective coatings on the teeth. For example U.S. Pat. No. 5,401,528 discloses the polymerisation of organically modified silicic acid polycondensates to coat the teeth; similarly U.S. Pat. No. 5,888,491 discloses the use of polymers grafted to polysiloxane chains for providing a highly substantive coating to the hard tissues within the oral cavity. However these complete coating systems are often unsuitable for home use, feel unnatural and the coating itself can still be subject to the deleterious effect of plaque-causing bacteria.

Silicones have a wide variety of uses in the dental industry including use as denture adhesive compositions (WO93/14737); non substantive neutral films (U.S. Pat. No. 5,032,387) and rubber materials for taking impressions (EP 822233). Furthermore it has long been recognised that polysiloxanes can be used within oral care compositions to provide a smooth, very thin water repellent coating to the teeth where they provide a hydrophobic surface and are thereby able to prevent the formation of caries and staining (GB 686,429, WO 93/23009 and WO95/03776). It has also been shown that, whilst the polysiloxane coating remains in place, it is able to act as a slow release reservoir for lipid soluble actives eg anti-bacterial agents (U.S. Pat. No. 5,422, 098). However, polysiloxanes themselves adhere to the teeth for only a short period of time so attempts have been made to enhance the substantivity by modifying the silicone oil for example by use of quaternised tertiary cyclic amines (GB 789,851); quaternary ammonium groups (U.S. Pat. No. 4,161,518) and aminoalkyl groups in conjunction with a lipophilic actives (EP 0,528,457). The initial work has been further extended with the applications WO 96/19190, WO 96/19191, WO 96/19192, and WO 96/19563 which disclose alkyl, alkoxy- and aminoalkyl-dimethicone copolyol oral compositions for use on teeth or acrylic surfaces of dentures comprising a wide range of dental actives. These compositions combine efficacy with substantivity, in-use performance characteristics and good cleaning properties. Furthermore, U.S. Pat. No. 5,057,307, U.S. Pat. No. 5,057, 309 and U.S. Pat. No. 5,733,529 disclose gels comprising a non-ionic surfactant, a coating material which is insoluble in that surfactant preferably polysiloxane polymers with a viscosity up to 50 million cps, viscosifiers, preferably cellulose ethers, and oral care actives such as stannous fluoride. Finally copending applications PCT/US99/15890 and PCT/US99/15891 (published as WO 01/01939 and WO 01/01940, respectively) disclose oral care compositions comprising an organosiloxane resin in combination with a volatile carrier capable of solubilising the resin and an oral care active for preparing compositions, which harden on the surface of the oral cavity. Whilst the compositions and disclosures of the prior art provide useful teaching for use of polysiloxanes in oral care compositions the approaches still have limitations. Overall there is no one composition which offers the combination of substantive and long term delivery of an oral care substance or active ingredient in conjunction with a product which is a non-drying composition which is easily applied to all surfaces of the oral cavity and which feels comfortable on the oral cavity surfaces, and which is able to be used for self treatment/home use and which is easy to remove.

Adhesive silicone systems are widely known including those which comprise a mixture of silicone gums with silicone resins in conjunction with a curing agent (eg catalysed condensation reactions, heating etc) and which are commonly referred to as pressure sensitive adhesives. Disclosures of such systems in the art include U.S. Pat. No. 4016328, U.S. Pat. No. 3,929,704, U.S. Pat. No. 2,814,601, U.S. Pat. No. 2,736,721, and CA 2085696. Such systems themselves are not suitable for home use in the oral cavity due to the harsh curing conditions that are required. However, attempts have been disclosed in the art to modify these systems such that their substantivity can be exploited in personal care products. Applications in this area include WO 93/17660, WO 98/16196, WO 97/17058 and WO 97/17059 which disclose the use of silicone resin:gum blends with volatile solvents in cosmetic compositions; WO 92/08439, U.S. Pat. No. 4,906,459, U.S. Pat. No. 4,902,499, WO 92/10161 and WO 92/10162 which disclose the use of silicone resin/gum/fluid blends in conjunction with surfactants as hair conditioning products; WO 00/06100, WO00/06107 which disclose the use of silicone resins in hair hold compositions; and GB 2,289,686 and U.S. Pat. No. 5,523, 017 which disclose translucent silicone emulsion systems for use in personal care products. Whilst the teachings of the prior art do provide useful advances in the use of silicone compositions in personal care products it does not sufficiently teach how to combine silicone gums, resins and fluids together to prepare non volatile, non hardening compositions which are substantive on the surface of the oral cavity and easily removed and which can optionally also be used for long term delivery of various oral care actives.

Surprisingly it has now been found that when a silicone resin is combined with a silicone gum and a non volatile polydimethylsiloxane fluid a composition is formed which can be readily applied to all surfaces of the oral cavity and which remains substantive on those surfaces. In addition, when oral care actives are included in these compositions the composition can be used to deliver sustained release of a wide range of oral care actives to the oral cavity throughout the wear duration. Furthermore because the composition comprises no volatile solvents it remains fluid on the teeth such that it is both particularly effective at delivering therapeutic agents interproximally, subgingivally and into certain periodontal pockets and furthermore retains consumer preferred aesthetics since the product does not form a hard coating on the surface of the teeth. Finally, because the film remains fluid it is easily removed by simple brushing and is therefore ideal for self administration by consumers. The invention can be further enhanced by optionally formulating it as a water in silicone emulsion wherein water soluble oral care actives can be dispersed within the water phase.

Without wishing to be bound by theory it is believed that the gum/resin mix creates a hydrophobic surface on the hard and soft tissues of the oral cavity which is able to both prevent build up of plaque and/or deliver oral care actives in a sustained manner. Furthermore it is believed that addition within the composition of the low viscosity fluid facilitates rapid wetting of surfaces of the composition, which both aids spreading of the compositions onto the surfaces of the oral cavity and also facilitates the manufacturing process. Finally it is believed if such a system is a water in silicone emulsion that, over time, the water phase gains weight as a result of the osmosis of water from the saliva into the internal water phase. This is believed to further enhance the substantivity of the composition to the surfaces of the oral cavity.

It is an object of the present invention to provide a substantive coating for the teeth which has acceptable mouth feel properties and which can prophylactically or therapeutically treat the surfaces of the oral cavity including by sustained release of an oral care active. Furthermore it is an object of the present invention to provide a substantive film for application to the oral tissues which does not dry over time and thus is easy to remove such that the film can be easily self administered by consumers.

These, and other objects of this invention, will become apparent in light of the following disclosure.

SUMMARY OF THE INVENTION

According to a first aspect the present invention relates to a non volatile composition that comprises:
  i) from about 0.5% to about 60%, by weight, of a silicone resin;
  ii) from about 0.1% to about 30%, by weight, of a silicone gum;
  iii) from about 0.1% to about 95%, by weight, of a non volatile polydimethylsiloxane fluid which has a viscosity from about 1 cStk to about 1000 cStk; and
  iv) from about 0.01% to about 50%, by weight, of an oral care active selected from teeth colour modifying substances, anti-tartar agents, anti-plaque agents, fluoride ion sources, anti-microbial agents, nutrients, antioxidants, H-2 antagonists, analgesics, anti-viral agents, mucosally absorbed pharmacological agents and mixtures thereof.

According to a second aspect the present invention relates to use of a non volatile oral care silicone composition in the oral cavity to treat the hard and soft tissue surfaces wherein the composition comprises:

i) from about 0.5% to about 60%, by weight, of a silicone resin;

ii) from about 0.1% to about 30%, by weight of a silicone gum;

iii) from about 0.1% to about 95%, by weight, of a non volatile polydimethylsiloxane fluid which has a viscosity from about 1 cStk to about 1000 cStk.

According to a third aspect the present invention relates to a non volatile composition that comprises:

i) from about 0.1% to about 30%, by weight, of a methyl substituted polyorganosiloxane gum with a viscosity of greater than about 500,000 cStk;

ii) a MQ polyorganosiloxane resin wherein the M:Q ratio is in the range of from about 0.6:1 to about 0.7:1;

iii) a non volatile polydimethylsiloxane fluid which has a viscosity from about 5 cStk to about 400 cStk; and wherein the weight ratio of polyorganosiloxane resin to polyorganosiloxane gum is in the range of from about 1:1 to about 7:1, wherein the weight ratio of polydimethylsiloxane fluid to polyorganosiloxane gum is in the range of from about 2:1 to about 8:1 and wherein the viscosity of the final composition is in the range of from about 1 Pa.s to about 1000 Pa.s.

DETAILED DESCRIPTION OF THE INVENTION

All percentages and ratios used herein are by weight of the total composition and all measurements made are at 25° C., unless otherwise designated. Unless otherwise indicated all percentages, ratios and levels of ingredients referred to herein are based on the actual amount of the ingredient, and do not include solvent, fillers or other materials which may be combined with the ingredient in commercially available products.

The term "oral care active" as used herein refers to any composition which has a prophylactic, therapeutic or cosmetic benefit either directly within the oral cavity or which is absorbed via the oral cavity but which has its primary benefit elsewhere. The term "treatment" as used herein refers to process of applying a substance to the oral cavity, wherein that substance may or may not comprise an oral care active, such that a prophylactic, therapeutic or cosmetic benefit is achieved.

The term "oral cavity" as referred to herein refers to the cavity from the lips to the epiglotis. The "hard tissues" comprise tissues such as the teeth and peridontal support and the like and the "soft tissues" comprise tissues such as the gums, the tongue, the surfaces of the buccal cavity and the like. Within the scope of this application the hard and soft tissues of the oral cavity should also be considered to comprise any devices which are used therein for example dentures, partial dentures, braces and the like.

The term "substantive" as used herein is understood to mean that sufficient quantities of the composition are retained in the oral cavity such that they can be perceived by the consumer either visually or by feel after a certain time period has elapsed. A guide to the expected in vivo substantivity of the compositions herein can be measured by an in vitro method. The method comprises using standard pharmaceutical disintegration apparatus, Erweka model ZT3-2, modified for gel applications. Briefly, a 50 $\mu$m film of bulk composition is formed on a glass microscope slide using a draw down bar. The slide with applied composition is continually dipped in and out of test solution (artificial saliva, 35° C.) over time; the weight of film is recorded at regular time intervals. Substantive compositions are defined as those retaining at least about 10%, preferably about 20% and more preferably about 50% of their original wet weight after about 2 hours exposure to solution has elapsed, preferably after about 4 hours has elapsed and more preferably after 6 hours has elapsed.

The term "safe and effective amount" as used herein means an amount of a compound, component, or composition sufficient to significantly induce a positive benefit but low enough to avoid serious side effects, i.e. to provide a reasonable benefit to risk ratio, within the scope of sound medical judgement.

The term "non volatile" as used herein means that the material referred to exhibits very low or no significant vapour pressure at ambient conditions, as well known and understood in the art. Non-volatile material will also generally have a boiling point at one atmosphere pressure of at least about 200° C., preferably at least about 275° C., and more preferably at least about 300° C. Furthermore this term means that the compositions comprise less than about 10%, preferably less than about 5% and more preferably less than about 2%, by weight, of a volatile material. As defined herein a volatile material is any material with a boiling point at one atmosphere of less than about 200° C.

Viscosities are measured using standard Brookfield viscometer techniques at room temperature which are known to those skilled in the art. The viscosities of the final products were measured at 25° C. using a Brookfield viscometer (model DV-II) using Spindle D at 10 rpm. Three reading were recorded at 1 min intervals, the average being taken as the viscosity measure of the sample.

Active and other ingredients useful herein may be categorised or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

General background material on silicones including sections discussion silicone fluids, gums and resins, as well as manufacture of silicones, can be found in *Encyclopaedia of Polymer Science and Engineering*, Volume 15, Second Edition, pp204–308, John Wiley & Sons Inc 1989 and *Chemistry and Technology of Silicones*, Walter Noll, Academic Press Inc, (Harcourt Brace Javanovich Publishers, New York), 1968, pp282–287 and 409–426, both incorporated herein by reference.

The elements of these compositions are described in more detail below.

Silicone Resins

Compositions for use in the present invention comprise from about 0.5% to about 60%, preferably from about 2% to about 50%, more preferably from about 10% to about 40% and most preferably from about 15% to about 25%, by weight, of a silicone resin.

Silicone resins as referred to herein are highly crosslinked polymeric siloxane systems. The crosslinking is introduced through the incorporation of tri-functional and tetra-functional silanes with mono-functional or di-functional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence a sufficient level of crosslinking) such that they dry down to a rigid or hard film are considered to be silicone resins. The ratio of oxygen atoms to silicone atoms is indicative of the level of crosslinking in a particular silicone material. Silicone materials which have at least about 1:1 oxygen atom per silicone atom will generally be silicone resins herein. Preferably, the ratio of oxygen: silicone atoms is at least about 1.2:1.0. Typical silanes used in the manufacture of silicone resins are the monomethyl, dimethyl, monophenyl, diphenyl, methylphenyl, monovinyl, and methylvinyl-chlorosilanes and tetrachlorosilanes. Preferred resins are the methyl, ethyl or phenyl substituted silicone resins. Commercially available silicone resins will generally be supplied in an unhardened form either as a powder or in a low viscosity volatile or, preferably non-volatile silicone fluid. It is preferred for use herein that the silicone resins are supplied as a powder or as a resin blend with a non volatile fluid.

Silicone resins can conveniently be identified according to a shorthand nomenclature system well known to those skilled in the art as the "MDTQ" nomenclature. Under this system, the silicone is described according to the presence of various siloxane monomer units which make up the silicone. Briefly, the symbol M denotes the mono-functional unit $((CH_3)_3SiO)_{0.5;}$ D denoted the di-functional unit $(CH_3)_2SiO$; T denotes the tri-functional unit $((CH)_3SiO)_{1.5}$; and Q denoted the quadra- or tetra-functional unit $SiO_2$. Note that a small amount of up to about 5% of silanol or alkoxy functionality may also be present in the resin structure as a result of processing. Primes of the unit symbols eg M', D', T', Q', denote substituents other than methyl, and must be specifically defined for each occurrence. Typical alternate substituents include groups such as vinyl, phenyl, amino, hydroxyl, etc. The molar ratios of the various units, either in terms of subscripts to the symbols indicating the total number of each type of unit in the silicone, or an average thereof, or as specifically indicated ratios in combination with molecular weight, complete the description of the silicone material under the "MDTQ" system. Higher relative amounts of T, Q, T', Q' to D, D', M, M' in a silicone resin is indicative of higher levels of crosslinking. As discussed before however, the overall level of crosslinking can also be indicated by the oxygen to silicone ratio.

The silicone resins preferred for use herein are MQ, MT, MTQ, and MDTQ resins; such MQ resins are disclosed in U.S. Pat. No. 5,330,747, Krysik issued Jul. 19, 1994. Thus the preferred silicone substituent is methyl. Especially preferred are MQ resins wherein the M:Q ratio is from about 0.4:1 to about 0.8:1, preferably from about 0.6:1 to about 0.7:1. The preferred silicone resins are solid at about 25° C. and the average molecular weight from abut 1,000 to about 10,000. The preferred resins are soluble in organic solvents such as toluene, xylene, isoparaffins and cyclosiloxanes and mixtures thereof. Organosiloxane resins such as these are commercially available, for example, SR 1000 and GE 1170-002, GE SS4230 and SS4267 from the General Electric Company and Wacker 803 and 804 available from Wacker Silicones Corporation of Adrian, Mich., U.S.

Silicone Gums

Compositions for use in the present invention comprise from about 0.1% to about 30%, preferably from about 1% to about 20%, more preferably from about 1% to about 10% and most preferably from about 2% to about 7%, by weight, of a silicone gum.

"Silicone gum" materials denote high molecular weight polydiorganosiloxanes having a viscosity at 25° C. of from about 500,000 cStk up to about 50,000,000 cStk. The viscosity of the material can be measured by means of a glass capillary viscometer as set forth in Dow Corning Corporation Test Method CTM004, Jul. 20, 1970. In addition silicone gums for use herein are considered to be polydiorganosiloxanes with an average molecular weight of greater than 500,000.

Silicone gums useful herein are described by Petrarch and others including U.S. Pat. No. 4,152,416 and Noll, Walter Chemistry and Technology of Silicones, New York Academic Press 1968. Also describing silicone gums are various General Electric Silicone Rubber Product Data Sheets. All of these described references are incorporated herein by reference.

The polysiloxane gums most suitable for use herein include those represented by the general formula (I):

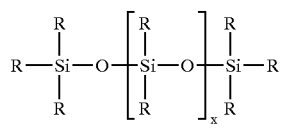

Formula I wherein each R independently is substituted or unsubstitued aliphatic (eg alkyl or alkenyl), aryl, alyloxy, alkylaryl, alkoxy, alkylamino (eg alkyl or alkenyl amino groups), hydroxy, or hydrogen or combinations thereof; and x is an integer sufficient such that the gum has the desired viscosity.

The polysiloxane gum for use herein can be linear or cyclic. Linear polysiloxanes are exemplified by Formula (I) above. Branched chain can also be used. Cyclic polysiloxanes include those represented by Formula (II):

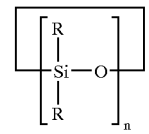

Formula II wherein R is as defined above and n is an integer sufficiently high such that the gum has the desired viscosity, preferably greater than about 500,000 cStk.

The substituents on the siloxane chain R may have any structure as long as the resulting polysiloxanes are hydrophobic, are neither irritating, toxic nor otherwise harmful when applied to human teeth, are capable of being deposited on human teeth, are compatible with the other components of the composition and are chemically stable under normal use and storage conditions.

Preferred alkyl and alkenyl substituents include C1–C5 alkyls and alkenyls, more preferably from C1–C4, most preferably from C1–C2. The aliphatic portions of other alkyl-, alkenyl-, or alkynyl-containing groups (such as alkoxy, alkylaryl and alkamino) can be straight or branched chains and preferably have from 1 to 5 carbon atoms, more preferably from 1 to 4 carbon atoms, even more preferably from 1 to 3 carbon atoms and most preferably from 1 to 2 carbon atoms. As discussed above the R substituents hereof can also contain amino functionalities eg alkamino groups which can be primary, secondary, tertiary amines or quarternary ammonium. These include mono, di, tri-alkylamino and alkoxyamino groups wherein the aliphatic portion chain length is preferably as described above. The R substituents can also be substitued with other groups, such as halogens (eg chloride, fluoride and bromide) halogenated aliphatic or aryl groups and hydroxy (eg hydroxy substitued aliphatic groups). Suitable halogenated R groups could include for example tri-halogenated (preferably fluoro) alkyl groups such as R1-C(F)$_3$, wherein R1 is C1–C3 alkyl. Preferred are methyl substituted polyorganosiloxane gums and methyl substituted polyorganosilanol gums.

Aryl containing substituents contain alicyclic and heterocyclic five and six membered aryl rings, and substituents continuing fused five or six membered rings. The aryl rings themselves can be substituted or unsubstituted. Substituents include aliphatic substituents and can also include alkoxy substituents, acyl substituents, ketones, halogens (e.g., chloride, fluoride and bromide), amines etc. Exemplary aryl-containing groups include substituted and unsubstituted alkyl or alkenyl substiuents eg allylphenyl, methyl phenyl, ethyl phenyl, vinyl phenyls such as styrenyl, and phenyl alkynes (eg phenyl C2–C4 alkynes). Heterocyclic aryl groups include substituents derived from furan, imadazole, pyrrole, pyridien etc. Fused aryl ring substituents include, for example, napthalene, couramin and purine.

Specific examples of preferred siloxane gums include polydimethylsiloxane, methylvinylsiloxane, copolymer, poly(dimethylsiloxane, diphenyl, methyvinylsiloxane) copolymer and mixtures thereof. The safety of polydimethylsiloxanes or use in these various products is well documented. See Rowe et al., *Journal of Industrial Hygiene*, 30:332–352 (1948). See also Calandra et al., *ACS Polymer Preprints*, 17:1–4 (1976) and Kennedy et al., *J. Toxicol. & Environmental Health*, 1:909–920 (1976). A highly preferred silicone gum is SE30 from General Electric.

For compositions for use herein it is highly preferred that the weight ratio between the silicone resin and the high molecular weight silicone gum is in the range of from about 0.1:1 to about 9:1, preferably from about 1:1 to about 7:1 and more preferably from about 1:1 to about 5:1.

Silicone Fluids

Compositions for use herein also comprise from about 0.1% to about 95%, preferably from about 5% to about 90%, more preferably from about 10% to about 85%, by weight of a non volatile polysiloxane fluid with a viscosity, at 25° C., of from about 1 cStk to about 1000 cStk, preferably from about 2 cStk to about 500 cStk and more preferably from about 5 cStk to about 400 cStk.

As for the gums, polysiloxane fluids for use herein can be linear or cyclic. They can be substituted with a wide variety of substituents. Any substituent already described above for the siloxane gums should also be considered to be useful as a substituent of the polysiloxane fluids. Preferred alkyl and alkenyl substituents include C1–C5 alkyls and alkenyls, more preferably from C1–C4, most preferably from C1–C2 and preferred aryl substituents are alicyclic and heterocyclic five and six membered aryl rings. Highly preferred substituents include methyl, ehtyl and phenyl substituents. Methyl is the most preferred substituent.

Suitable polysiloxane fluids include linear polysiloxane polymers such as dimethicone and other low viscosity analogues of the polysiloxane materials, preferably having a viscosity at 25° C. of 200 cStk or less and cyclomethicone, and other cyclic siloxanes having for example a viscosity at 25° C. of 200 cStk or less. Commercial examples of materials that are suitable for use herein include DC200 series fluids from Dow Corning and the AK Fluid series from Wacker Silicones.

It is preferred that for compositions for use herein that the weight ratio between the low viscosity polysiloxane fluid and the high viscosity polysiloxane gum is in the range of from about 0.1:1 to about 20:1, preferably from about 1:1 to about 10:1 and more preferably from about 2:1 to 8:1 and even more preferably from about 2:1 to about 5:1.

Oral Care Actives

According to a first aspect of the invention the compositions herein comprise from about 0.01% to about 50%, preferably from about 0.01% to about 20%, more preferably from about 0.01% to about 10%, by weight, of an oral care active selected from teeth colour modifying substances, anti-tartar agents, anti-plaque agents, fluoride ion sources, anti-microbial agents, nutrients, antioxidants, H-2 antagonists, analgesics, anti-viral agents, mucosally absorbed pharmacological agents and mixtures thereof. The oral care actives preferably contain an active at a level where upon directed use, the benefit sought by the wearer is promoted without detriment to the oral surface to which it is applied.

Oral care compositions or substances of the present invention may include many of the actives previously discussed in the art. The following is a non-limiting list of oral care actives that may be used in the present invention:

1. Teeth Colour Modifying Substances Teeth colour modifying substances may be considered among the oral care actives useful in the present invention. These substance are suitable for modifying the colour of the teeth to satisfy the consumer. These substances could be particles that when applied on the tooth surface modify that surface in terms of absorption and, or reflection of light. Such particles provide an appearance benefit when a file containing such particles is applied over the surfaces of a tooth or teeth. This benefit may last to the point wherein the film has eroded, or been removed, presenting for example a mottled or uniform looking tooth surface.

Particles most useful in the present invention include pigments and colourants routinely used in the cosmetic arts. There are no specific limitations as to the pigment and, or colourant used in compositions of the present invention other than the limitation of the effect it has on the light source upon the teeth surfaces. Pigments and colourants include inorganic white pigments, inorganic coloured pigments, pearling agents, filler powders and the like; see Japanese Published Patent Application Kokai No 9 [1997]-100215, published Apr. 15, 1997, incorporated herein by reference. Specific examples are selected from the group consisting of talc, mica, magnesium carbonate, calcium carbonate, magnesium silicate, aluminium magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Most preferred are those selected from the group consisting of titanium dioxide, bismuth oxychloride, zinc oxide and mixtures thereof. Pigments that are generally recognised as safe, and are listed in the *CTFA Cosmetic Ingredient Handbook, 3$^{rd}$ Edition*, Cosmetic and Fragrances Association Inc., Washington D.C. (1982), incorporated herein by reference.

The pigments are typically used as opacifiers and colourants. These pigments can be used as treated particles, or as the raw pigments themselves. Typical pigment levels are selected for the particular impact that is desirable by the consumer. For example, for teeth that are particularly dart or stained one would typically use pigments in sufficient amount to lighten the teeth. On the other hand, where individual teeth or spots on the teeth are lighter that other teeth, pigments to darken the teeth may be useful. The levels of pigments and colourants are generally used in the range of about 0.05% to about 20%, preferably from about 0.1% to about 15% and most preferably from about 0.25% to about 10%, by weight, of the composition. It is highly preferred that when a composition for use herein comprises a pigment it additionally comprises a further oral care active.

Compositions for use herein may also comprise materials that remove or bleach intrinsic or extrinsic stains on or in tooth surfaces. Such substance are selected from the group consisting of the peroxides, metal chlorites, perborates, percarbonates, peroxyacids, persulphates, and combinations thereof. Suitable peroxide compounds include hydrogen peroxide, urea peroxide, calcium peroxide, carbamide peroxide and mixtures thereof. Most preferred is carbamide peroxide. Suitable metal chlorites include calcium chlorite, barium chlorite, magnesium chlorite, lithium chlorite, sodium chlorite and potassium chlorite. Additional bleaching substances may be hypochlorite, and chlorine dioxide. The preferred chlorite is sodium chlorite. A preferred percarbonate is sodium percarbonate. Preferred persulphates are oxones. The level of these substances is dependent on the available oxygen or chlorine respectively that the molecule is capable of providing to bleach the stain. This level is generally used in compositions of the present invention at levels from about 0.1% to about 35%, preferably from about 1% to about 25% and most preferably from about 5% to about 10% of the composition.

2. Anti-tartar Agents Anti-tartar agents known for use in dental care products include phosphate Phosphates include pyrophosphates, polyphosphates, polyphosphonates and mixtures thereof. Pyrophosphates are among the best known for use in dental care products but polyphosphates are also considered to be highly useful in the compositions of the present invention. The pyrophosphate salts useful in the present compositions include the dialkali metal pyrophosphate salts, tetra-alkali metal pyrophosphate salts and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) and mixtures thereof, in their unhydrated as well as hydrated forms are the preferred species. While any of the above mentioned pyrophosphate salts may be used, tetrasodium pyrophosphate salt is preferred. Sodium polyphosphate and triethanolamine polyphosphates, for example, are preferred.

The pyrophosphate salts are described in more detail in *Kirk and Othmer, Encyclopedia of Chemical Technology, 3rd* Edition, Volume 17, Wiley Interscience Publishers (1982). Additional anticalculus agents include pyrophosphates or polyphosphates disclosed in U.S. Pat. No. 4,590,066 issued to Parran and Sakkab on May 20, 1986; polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict and Sunberg on Apr. 28, 1987; polyepoxysuccinates such as those disclosed in U.S. Pat. No. 4,846,650 issued to Bendict, Bush and Sunberg on Jul. 11, 1989; ethylenediaminetetraacetic acid as disclosed in British Patent No 490,384 date Feb. 15, 1937; nitrilotriacetic acid and related compounds as disclosed in U.S. Pat. No. 3,678,154 issued to Widder and Briner on Jul. 18, 1972; polyphosphonates as disclosed in U.S. Pat. No. 3,737,533 issued to Francis on Jun. 5, 1973; U.S. Pat. No. 3,988,443 issued to Ploger, Schmidt-Dunker and Gloxhuber on Oct. 26, 1976 and U.S. Pat. No. 4,877,603 issed to Degenhardt and Kozikowski on Oct. 31, 1989. Anticalculus phosphates include potassium and sodium pyrophosphates; sodium tripolyphosphate; diphosphonates such as ethane-1-hydroxy-1,1-diphosphonate, 1-azacycloheptane-1, 1-diphosphonate, and linear alkyl disphosphonates; linear carboxylic acids; and sodium zinc citrate and other soluble zinc salts.

Polyphosphates preferred are those having a chain length of three or more, especially those with a chain length of around four or more phosphate molecules including tetrapolyphosphate and hexametaphosphate, among others. Polyphosphates larger than tetrapolyphosphate usually occur as amorphous glassy materials. Preferred in this invention are the linear "glassy" polyphosphates having the formula:

wherein X is sodium, potassium, or hydrogen and n averages from about 6 to about 125. Most preferred is a particulate sodium polyphosphate with an average chain length of from about 10 to about 30, preferably from about 15 to 25, more preferably from about 21 to about 23. Such polyphosphates are manufactured by FMC Corporation and are commercially known as Sodaphos (n≈6), Hexaphos (n≈13), and Glass H (n≈21). Hexaphos and Glass H are preferred with Glass H being the most preferred polyphosphate. These polyphosphates may be used alone or in a combination thereof.

Agents that may be used in place of, or in combination with, the pyrophosphate salt include such known materials as synthetic anionic polymers including polyacrylates and copolymers of maleic anhydride or acid and methyl vinyl ether (eg Gantrez), as described, for example in U.S. Pat. No. 4,627,977 to Gaffer et al; as well as eg polyamino propane sulphonic acid (AMPS), zinc citrate trihydrate, polyphosphates (eg tripolyphosphate; hexametaphosphate), diphosphonates (eg EHDP; AHP), polypeptides (such as polyaspartic and polyglutamic acids) and mixtures thereof.

3. Anti-Plaque Agents Anti-plaque agents are any substances which inhibit the accumulation of bacterial deposits on the surfaces of the oral cavity. Examples include xylitol and other anti-microbial agents.

4. Fluoride Ion Source Fluoride ion sources are well known for use in oral care compositions as anticaries agents. Fluoride ions are contained in a number of oral care compositions for this purpose, particularly toothpastes. Patents disclosing such toothpastes include U.S. Pat. No. 3,538,230, Nov. 3, 1970 issued to Pader et al; U.S. Pat. No. 3,689,637, Sep. 5th, 1972 to Pader; U.S. Pat. No. 3,711,604, Jan. 16, 1973 to Colodney et al; U.S. Pat. No. 3,911,104 Oct. 7, 1975 to Harrison; U.S. Pat. No. 3,935,306, Jan. 26, 1976 to Roberts et al; and U.S. Pat. No. 4,040,858 Aug. 9, 1977 to Wasson.

Application of fluoride ions to dental enamel serves to protect teeth against decay. A wide variety of fluoride ion yielding materials can be employed as sources of soluble fluoride in the present compositions. Examples of suitable fluoride ion yielding materials are found in U.S. Pat. No. 3,535,421, Oct. 20, 1970 issued to Briner et al and U.S. Pat. No. 3,678,154 Jul. 18, 1972 issued to Widder et al. Preferred fluoride ion sources for use herein include sodium fluoride, potassium fluoride, stannous fluoride, ammonium fluoride and mixtures thereof. Sodium fluoride is particularly preferred. Preferably the present composition provide from about 50 ppm to about 10,000 ppm, more preferably from about 100 ppm to about 3000 ppm of fluoride ions in the compositions that contact dental surfaces when used with the delivery system of the present invention.

5. Anti Microbial Agents Antimicrobial agents can also be present in the oral care compositions or substances of the present invention. Such agents may include, but are not limited to, 5-chloro-2-(2,4-dichlorophenoxy)-phenol, commonly referred to as triclosan, and described in the Merck Index, 11th Edition, (1989), pp1529 (entry no 9573) in U.S. Pat. No. 3,506,720, and in European Patent Application No 0,251,591 of Beecham Group, Plc, published Jan. 7th, 1988; phthalic acid and its slats including, but not limited to those disclosed in U.S. Pat. No. 4,994,262 published Feb. 19th, 1991, preferably magnesium mono-potassium phthalate, chlorhexidine (Merck Index, no 2090); alexidine (Merck Index, no 222); hexetidine (Merck Index, no 4624); sanguinarine (Merck Index, no 8320); benzalkonium chloride (Merck Index, no 1066); salicylanilide (Merck Index, no 8299); domiphen bromide (Merck Index, no 3411); cetylpyridinium chloride (CPC) (Merck Index, no 2024); tetradecylpyridinium chloride (TPC); N-tetradecyl-4-ethylpyridinium chloride (TDEPC); octenifine; delmopinol; octapinol; and other piperidine derivatives; nicin preparations; zinc/stannous ion agents; antibiotics such as augmentin, amoxicilline, tetracycline, doxycycline, minocycline, and metronidazole; and analogues and salts of the above; essential oils including thymol, geraniol, carvacrol, citral, hinokitiol, eucalyptol, catechol (particularly 4-allyl catechol) and mixtures thereof; methyl salicyclate; hydrogen peroxide; metal salts of chlorite and mixtures of all of the above.

6. Nutrients Nutrients may improve the condition of the oral cavity and can be include in the oral care compositions or substances of the present invention. Nutrients include minerals, vitamins, oral nutritional supplements, enteral nutritional supplements, herbal supplements, natural extracts and mixtures thereof.

Minerals that can be included with the compositions of the present invention include calcium, phosphorus, fluoride, zinc, manganese, potassium and mixtures thereof. These minerals are disclosed in Drug Facts and Comparisons (loose leaf drug information service), Wolters Kluer Company, St Louis, Mo., ©1997, pp10–17.

Vitamins can be included with minerals or used separately. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in Drug Facts and Comparisons (loose leaf drug information service), Wolters Kluer Company, St Louis, Mo., ©1997, pp3–10.

Oral nutritional supplements include amino acids, lipotropics, fish oil, coenzyme Q10, and mixtures thereof, as disclosed in Drug Facts and Comparisons (loose leaf drug information service), Wolters Kluer Company, St Louis, Mo., ©1997, pp54–54e. Amino acids include, but are not limited to L-tryptophane, L-lysine, methionine, threonine, levocarnitine or L-carnitine and mixtures thereof. Lipotropics include, but are not limited to choline, inositol, betaine, linoleic acid, linolenic acid and mixtures thereof. Fish oil contains large amounts of Omega-3 (N-3) polyunsaturated fatty acids, eicosapentaenoic acid and docosahexaenoic acid.

Entenal nutritional supplements include, but are not limited to, protein products, glucose polymers, corn oil, safflower oil, medium chain triglycerides as disclosed in *Drug Facts and Comparisons* (loose leaf drug information service), Wolters Kluer Company, St Louis, Mo., ©1997, pp55–57.

7. Antioxidants Antioxidants are generally recognised as useful in compositions such as those of the present invention. Antioxidants are disclosed in texts such as Cadenas and Packer, *The Handbook of Antioxidants*, ©1996 by Marcel Dekker, Inc. Antioxidants that may be included in the oral care compositions of the present invention include, but are not limited to, Vitamin E, ascorbic acid, Uric acid, carotenoids, Vitamin A, flavenoids and polyphenols, herbal antioxidants, melatonin, aminoindoles, lipoic acids and mixtures thereof.

8. H-2 Antagonists Histamine-2 (H-2) receptor antagonist compounds (H-2 antagonists) may be used in the oral care compositions of the present invention. As used herein, selective H-2 antagonists are compounds that block H-2 receptors, but do not have meaningful activity in blocking histamine-1 (H-1) receptors. Selective H-2 antagonists stimulate the contraction of smooth muscle from various organs, such as the gut and bronchi; this effect can be suppressed by low concentrations of mepyramine—a typical antihistaminic drug. The pharmacological receptors involved in these mepyramine-sensitive histamine responses have been defined as H-1 receptors (Ash, A. S. F & Schild H. O, *Brit J Pharmacol Chem* 1966, Vol 27, p427). Histamine also stimulates the secretion of acid by the stomach (Loew E R & Chickering O, *Proc Soc Exp Biol Med*, 1941, Vol 48, p65), increases the heart rate (Trendelenburg U *J. Pharmacol* 1960, Vol 130 p450) and inhibits contractions in the rat uterus (Dews P B & Graham J D P, *Brit J. Pharmacol Chem*, 1946, Vol 1, p278); these actions cannot be antagonised by mepyramine and related drugs. The H-2 antagonists useful in the oral care compositions or substances are those that blockade the receptors involved in mepyramine insensitive, non H-1 (H-2), histamine responses and do not blockade the receptors involved in mepyramine-sensitive histamine responses.

Selective H-2 antagonists are those compounds found to be H-2 antagonists through their performance in classical pre-clinical screening tests for H-2 antagonist function. Selective H-2 antagonists are identified as compounds which can be demonstrated to function as competitive or non-competitive inhibitors of histamine mediated effects in those screening models specifically dependent upon H-2 receptor function, but to lack significant histamine antagonist activity in those screening models dependent upon H-1 receptor function. Specifically, this includes compounds that would be classified as described by Black J W, Duncan W A M, Durant C J, Ganelline C R and Parsons E M, "Definitions and Antagonism of Histamine H2-Receptors", *Nature* 1972, vol 236 pp 385–390, as H-2 antagonists if assessed as described by Black through testing with the guinea pig spontaneously beating right atria in vitro assay and the rat gastric acid secretion in vivo assay, but shown to lack insignificant H-1 antagonist activity relative to H-2 antagonist activity, if assessed as described by Black with either the guinea pig ileum contraction in vitro assay or the rat stomach muscle contraction in vivo assay. Preferably selective H-2 antagonists demonstrate no significant H-1 activity at reasonable dosage levels in the above H-1 assays. Typical reasonable dosage level is the lowest dosage level at which 90% inhibition of histamine, preferably 99% inhibition of histamine, is achieved in the above H-2 assays.

Selective H-2 antagonists include compounds meeting the above criteria which are disclosed in U.S. Pat. Nos. 5,294, 433 and 5,364,616 to Singer et al., issued Mar. 15, 1994 and Nov. 15, 1994 respectively and assigned to Procter & Gamble, wherein the selective H-2 antagonist is selected from the group consisting of cimetidine, etintidine, ranitidine, ICIA-5165, tiotidine, ORF-17578, lupititidine, donetidine, famotidine, roxatidine, pifatidine, lamtidine, BL-6548, BMY-25271, zaltidine, nizatidine, mifentidine, BMY-52368, SKF-94482, BL-6341A, ICI-162846, ramixotidine, Wy-45727, SR-58042, BMY-25405, loxtidine, DA-4634, bisfentidine, sufotidine, ebrotidine, HE-30-256, D-16637, FRG-8813, FRG-8701, impromidine, L-643728 and HB-408.4. Particularly preferred is cimetidien (SKF-92334), N-cyano-N'-methyl-N"-(2-(((5-methyl-1H-imidazol-4-yl)methyl)thio)ethyl)guanidine:

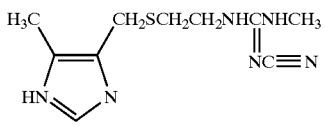

Cimetidine is also disclosed in the Merck Index, 11$^{th}$ edition (1989), p354 (entry no 2279), and *Physicians' Desk Reference*, 46$^{th}$ edition (1992), p2228. Related preferred H-2 antagonists include burimamide and metiamide.

9. Analgesics Anti-pain or desensitising agents can also be present in the oral care compositions or substances of the present invention. Such agents may include, but are not limited to, strontium chloride, potassium nitrate, natural herbs such as gall nut, Asarum, Cubebin, Galanga, scutellaria, Liangmianzhen, Baizhi, etc. Analgesics also include the anti-inflammatory agents. Such agents may include, but are not limited to, non-steroidal anti-inflammatory agents of NSAIDs, such as ketorolac, flurbinprofen, ibuprofen, naproxen, indomethacin, aspirin, ketoprofen, piroxicam and meclofenamic acid. Use of NSAIDs such as Ketorolac are claimed in U.S. Pat. No. 5,626,838, issued May 6, 1997. Disclosed therein are methods of preventing and, or treating primary and reoccurring squamous cell carcinoma of the oral cavity or oropharynx by topical administration to the oral cavity or oropharynx an effective amount of an NSAID.

10. Anti-Viral Agents Anti-viral actives useful in the present composition include any known actives that are routinely used to treat viral infections. Such anti-viral actives are disclosed in Drug Facts and Comparisons (Loose leaf drug information service), Wolters Kluer Company, St. Louis, Mo., ©1997, pp 402(a)-407(z), incorporated herein by reference in its entirety. Specific examples include anti-viral actives disclosed in U.S. Pat. No. 5,747,070 issued May 5, 1998 to Satyanarayana Majeti, incorporated herein by reference in its entirety. Said patent discloses the use of stannous salts to control viruses. Stannous salts and other anti-viral actives are described in detail in *Kirk and Othmer, Encyclopedia of Chemical Technology*, 3$^{rd}$ Edition, vol 23, Wiley Interscience Publishers (1982), pp42–71, incorporated herein by reference in its entirety. The stannous salts that may be used in the present invention would include organic stannous carboxylates and inorganic stannous halides. While stannous fluoride may be used, it is typically used only in combination with another stannous halide or one or more stannous carboxylates or another therapeutic agents.

11. Mucosally Absorbed Pharmacological Agents Antitussives are actives particularly useful for arresting uncontrollable fits of coughing. Antitussives useful in the present invention include, but, are not restricted to, the group consisting of codeine, dextromethorphan, dextrorphan, diphenhydramine, hydrocodone, noscapine, oxycodone, pentoxyverine, pholcodine and mixtures thereof. Of these antitussives, dextromethorphan is preferred. Safe and effective amounts of other cough/cold drug actives may be included in such dextromethorphan-containing compositions. Particularly useful are the actives that are suited for absorption through the mucosal tissues as described in J. G. Hardman, *The Pharmacologic Basis of Therapeutics*, Ninth Edition, McGraw-Hill, New York, 1995. Other actives which are absorbed through the mucosal membrane include antihistamines; non-sedating antihistamines; decongestants; expectorants; mucolytics, analgesic, antipyretic anti-inflammatory agents, local anesthetics and mixtures thereof. As such these actives may also be incorporated into compositions of the present invention.

Other Ingredients

In addition these oral care products can contain a variety of nonessential optional components suitable for rendering such compositions more acceptable. Such conventional optional ingredients are well known to those skilled in the art eg preservatives such as benzyl alcohol, methyl paraben, propyl paraben and imidiazolindinyl urea; cationic surfactants such as cetyl trimethylammonium chloride, lauryl trimethyl ammonium chloride, tricetyl methyl ammonium chloride and di(partially hydrogentated tallow) dimethylammonium chloride; thickeners and viscosity modifiers such as diethanolamide of long chain fatty acid (eg PEG 3 lauramide), block polymers of ethylene oxide and propylene oxide such as Pluronic F88 offered by BASF Wyandotte, sodium chloride, sodium sulphate, polyvinyl alcohol, and ethyl alcohol; pH adjusting agents and buffering agents such as citric acid, succinic acid, phosphoric acid, sodium hydroxide, sodium carbonate etc; sweetening agents; flavouring agents such as oil of peppermint, oil of sassafras, clove bud oil, peppermint, menthol, anethole, thymol, methylsalicylate, eucalyptol, cassia, 1-menthyl acetate, sage, eugenol, parsely oil, oxanone, oil of wintergreen, alpha-irisone, oil of spearmint, marjoram, lemon, orange, propenyl guaethol, cinnamon, and mixtures thereof; perfumes; dyes; and sequestering agents such as disodium ethylenediamine tetraacetate. Such agents are generally used individually at a level of from about 0.001% to about 10%, preferably from about 0.5% to about 5.0%, by weight, of the composition.

Compositions for use herein may comprise less than about 10%, preferably less than about 5% and more preferably less than about 2%, by weight, of volatile solvents. As defined herein volatile solvents refer to any material, organic or silicone in origin, which has a boiling point of about 200° C., or less, at one atmosphere pressure.

Furthermore compositions herein are intended to be used without the need for curing, either hot curing or cold curing. As such it is intended that compositions of the present invention are used alone and without any additional curing agent.

According to the third aspect of this invention the compositions have a viscosity of from about 1 Pa.s to about 1000 Pa.s. For all aspects of this invention it is preferred that the compositions have a viscosity of from about 2 Pa.s to about 500 Pa.s, preferably from about 5 Pa.s to about 300 Pa.s and more preferably from about 10 Pa.s to about 250 Pa.s.

Rheology Modifiers

The compositions of the present invention can optionally comprise a rheology modifier which inhibits settling and separation of component s or control settling in a manner which facilitates re-dispersion and may control rheological flow properties. Suitable rheology modifiers herein include organo modified clays, silicas, cellulose polymers such as hydroxypropylmethyl cellulose, xanthan gum, carbomers, inorganic clay polymers, polycarboxylates, EO/PO block copolymers (poloxamers) thickening silicas and mixtures thereof. The preferred organophilic clays comprise Quaternium-18 hectorite or Stearalkonium hectoriate, such as Bentone 27 and 38 from Rheox, organoclay dispersion such as Bentone ISD Gel; or bentonites organo modified clays such as Bentone 34 from Rheox or the Claytone Series from Southern Clay Products; and mixtures thereof. The preferred silicas may be fumed silica such as the Aerosil series from Degussa or the Cab-o-Sil series from Cabot Corporation, silica gels such as the Sylodent or Sylox series from W R Grace & Co or precipitated silica such as Zeothix 265 from J. M. Huber Corporation. The rheology modifier is preferably present in the composition at a level of from about 0.1% to about 15%, preferably from about 0.5% to about 10%, and even more preferably from about 1% to about 3%, by weight, of the composition.

Carrier

Compositions for use herein can take a variety of forms for example single phase silicone systems, an emulsion system such as a water in silicone emulsion or an oil in silicone emulsion or a dispersion. The advantage of combining an additional phase into compositions of the present invention is that the additional phase can be used to solubilise additional ingredients for example oral care actives, which are not naturally soluble in silicone systems. It is highly preferred that the compositions for use herein are water in silicone emulsions, or water in silicone dispersion, wherein the internal water phase comprises from about 5% to about 95%, preferably from about 25% to about 75%, more preferably from about 30% to about 60%, by weight, of the final composition. Furthermore it is preferred that such a system comprises from about 0.001% to about 90%, preferably from about 5% to about 75%, even more preferably from about 10% to about 60%, by weight, of water. Furthermore it is preferred that if the composition is a water in silicone emulsion or dispersion that the internal aqueous phase comprises rheology modifiers.

Preparation of Compositions

The compositions of the present invention are prepared by standard techniques well known to those skilled in the art. If the composition comprises more than one phase, in general the different phases will be prepared separately, with materials of similar phase partitioning being added in any order. The two phases will then be combined with vigorous stirring to form the multiphase system eg an emulsion or dispersion. Any ingredients in the formulation with high volatility, or which are susceptible to hydrolysis at high temperatures, will usually be added post mixing of the different phases with gentle stirring.

Method of Use

A second aspect of this invention relates to the use of a non volatile oral care silicone composition in the oral cavity to form a hydrophobic layer on the hard and soft tissue surfaces wherein the composition comprises:

i) from about 0.5% to about 60%, by weight, of a silicone resin;

ii) from about 0.1% to about 30%, by weight of a silicone gum;

iii) from about 0.1% to about 95%, by weight, of a non volatile polysiloxane fluid which has a viscosity from about 1 cStk to about 1000 cStk.

Compositions of the present invention are applied to the surfaces of the oral cavity either by use of an applicator or by use of the finger. Compositions can either be applied to one or more particular areas of the oral cavity or broadly applied to the whole cavity. Due to the wetting properties of the compositions, once applied, they will rapidly spread to cover a wide area. As a result compositions can be used to coat hard to reach areas of the oral cavity such as interdental pockets, subgingival cavities and the like. Furthermore, as a result of the substantivity of the compositions herein they will remain in place on the surfaces of the oral cavity for at least about 2 hours, preferably about 4 hours, more preferably about 6 hours and most preferably about 8 hours. Compositions are then easily removed from the cavity by normal oral hygiene techniques such as brushing without damaged to the tissues of the oral cavity.

EXAMPLES

The following examples further illustrate the preferred embodiments within the scope of the present invention. These examples are given solely for the purpose of illustration and are not to be construed as limitations of the present invention as many variations of the invention are possible without departing from its spirit or scope. Unless otherwise indicated, all ingredients are expressed as a weight percentage of the composition.

Example 1

| INGREDIENT | % w/w |
|---|---|
| Silicone resin (SR1000; GE Silicones)[1] | 30.00 |
| Silicone gum (SE30; GE Silicones)[1] | 10.00 |
| Silicone fluid (DC200 350 cStk; Dow Corning)[2] | 60.00 |
| TOTAL | 100.00 |

Using an overhead mixer, slowly add silicone gum to pre-weighed silicone fluid. Once uniformly mixed, slowly add in resin under mixing until composition appears visually clear.

Example 2

| INGREDIENT | % w/w |
|---|---|
| Silicone resin (TMS 803, Wacker Chemicals)[3] | 32.00 |
| Silicone gum/fluid blend (CF1251; GE Silicones)[1] | 53.33 |
| Silicone fluid (DC200 350 cStk; Dow Corning)[2] | 14.67 |
| TOTAL | 100.00 |

Using an overhead mixer, slowly add silicone resin to pre-weighed silicone fluid/gum blend till uniformly mixed and composition appears visually clear.

Example 3

| INGREDIENT | % w/w |
|---|---|
| Silicone resin (SR1000; GE Silicones)[1] | 35.00 |
| Silicone gum/fluid blend (CF1251; GE Silicones)[1] | 64.70 |
| Triclosan | 0.30 |
| TOTAL | 100.00 |

Using an overhead mixer, slowly add silicone resin to pre-weighed silicone fluid/gum blend till uniformly mixed and composition appears visually clear.

Example 4

| INGREDIENT | % w/w |
| --- | --- |
| Silicone resin (SR1000; GE Silicones)[1] | 19.82 |
| Silicone gum/fluid blend (SF1236; GE Silicones)[1] | 33.31 |
| Silicone fluid (DC200 100 cStk; Dow Corning)[2] | 8.47 |
| Water | 28.30 |
| Xylitol | 10.00 |
| Methyl/Propyl parabens | 0.10 |
| TOTAL | 100.00 |

Using an overhead mixer, add silicone fluid to silicone gum/fluid blend. Slowly add silicone resin to pre-weighed silicone fluid/gum blend till uniformly mixed and composition appears visually clear. Separately, dissolve xylitol and parabens in water. Add into silicone premix under strong mixing.

Example 5

| INGREDIENT | % w/w |
| --- | --- |
| Silicone resin (SR1000; GE Silicones)[1] | 20.00 |
| Silicone gum/fluid blend (SF1236; GE Silicones)[1] | 33.31 |
| Silicone fluid (DC200 350 cStk; Dow Corning)[2] | 8.29 |
| Triclosan | 0.30 |
| Water | 28.00 |
| Xylitol | 10.00 |
| Methyl/Propyl parabens | 0.10 |
| TOTAL | 100.00 |

Using an overhead mixer, add silicone fluid to silicone gum/fluid blend. Slowly add silicone resin (with triclosan pre-dispersed therein) to pre-weighed silicone fluid/gum blend till uniformly mixed and composition appears visually clear. Separately, dissolve xylitol and parabens in water. Add into silicone premix under strong mixing.

Example 6

| INGREDIENT | % w/w |
| --- | --- |
| Silicone resin (SR1000; GE Silicones)[1] | 10.00 |
| Silicone gum/fluid blend (SF1236; GE Silicones)[1] | 33.31 |
| Silicone fluid (DC200 350 cStk; Dow Corning)[2] | 7.99 |
| Triclosan | 0.30 |
| Water | 30.00 |
| Xylitol | 10.00 |
| Glycerin | 8.00 |
| Xanthan Gum (Ketrol 1000)[4] | 0.30 |
| Methyl/Propyl parabens | 0.10 |
| TOTAL | 100.00 |

Using an overhead mixer, add silicone fluid to silicone gum/fluid blend. Slowly add silicone resin (with triclosan pre-dispersed therein) to pre-weighed silicone fluid/gum blend till uniformly mixed and composition appears visually clear. Separately, dissolve xylitol and parabens in water. Add into silicone premix under strong mixing. Predisperse Xanthan gum in glycerin and add to bulk under strong mixing.

Example 7

| INGREDIENT | % w/w |
| --- | --- |
| Silicone resin (SR1000; GE Silicones)[1] | 10.00 |
| Silicone gum/fluid blend (SF1236; GE Silicones)[1] | 33.31 |
| Silicone fluid (DC200 350 cStk; Dow Corning)[2] | 7.89 |
| Triclosan | 0.30 |
| Water | 30.00 |
| Xylitol | 10.00 |
| Glycerin | 8.00 |
| Xanthan Gum (Ketrol 1000)[4] | 0.30 |
| Pemulen TR2 (BF Goodrich)[5] | 0.10 |
| Methyl/Propyl parabens | 0.10 |
| TOTAL | 100.00 |

Using an overhead mixer, add silicone fluid to silicone gum/fluid blend. Slowly add silicone resin (with triclosan pre-dispersed therein) to pre-weighed silicone fluid/gum blend till uniformly mixed and composition appears visually clear. Separately, disperse Pemulen in water under strong mixing. Dissolve xylitol and parabens in water/pemulen mix. Add into silicone premix under strong mixing. Predisperse Xanthan gum in glycerin and add to bulk under strong mixing.

Example 8

| INGREDIENT | % w/w |
| --- | --- |
| Silicone resin (TMS 803; Wacker Silicones)[3] | 10.00 |
| Silicone gum/fluid blend (DC Q2 1403; Dow Corning)[1] | 38.46 |
| Triclosan | 0.30 |
| Water | 32.64 |
| Xylitol | 10.00 |
| Glycerin | 8.00 |
| Xanthan Gum (Ketrol 1000)[4] | 0.30 |
| Pemulen TR2 (BF Goodrich)[5] | 0.10 |
| Methyl/Propyl parabens | 0.10 |
| TOTAL | 100.00 |

[1]GE Silicones 260 Hudson River Road, Waterford, New York 12188, USA
[2]Dow Corning 62, Rue General De Gaulle, 1310 La Hulpe, Brussels, Belgium
[3]Wacker-Chemie GmbH, Silicones Division, Haans-Seidel-Platz 4, D-81737 Muchen, Germany
[4]Kelco Dorset House, Regent Park, Kingston Road, Leatherhead, Surrey KT22 7PL, UK
[5]BF Goodrich Rue de Vendunstraat, 742, B-1130, Brussels, Belgium Using an overhead mixer, add silicone resin to gum/fluid blend (with triclosan pre-dispersed therein) till uniformly mixed and composition appears visually clear. Separately, disperse Pemulen in water under strong mixing. Dissolve xylitol and parabens in water/pemulen mix. Add into silicone premix under strong mixing. Predisperse Xanthan gum in glycerin and add to bulk under strong mixing.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A non volatile composition that comprises:
   i) from about 0.5% to about 60%, by weight, of a silicone resin;
   ii) from about 0.1% to about 30% by weight, of a silicone gum;
   iii) from about 0.1% to about 95%, by weight, of a non volatile polysiloxane fluid which has a viscosity from about 1 cStk to about 1000 cStk; and
   iv) from about 0.01% to about 50%, by weight, of an oral care active selected from the group consisting of teeth color modifying substances, anti-tartar agents, anti-plaque agents, fluoride ion sources, anti-microbial agents, nutrients, antioxidants, H-2 antagonists, analgesics, anti-viral agents, mucosally absorbed pharmacological agents and mixtures thereof.

2. A composition according to claim 1 wherein the silicone resin is selected from MQ resins with an M:Q ratio of from about 0.4:1 to about 0.8:1.

3. A composition according to claim 1 which comprises from about 2% to about 50%, of silicone resin.

4. A composition according to claim 1 which comprises from about 1% to about 20%, by weight, silicone gum.

5. A composition according to claim 1 wherein the polysiloxane fluid has a viscosity from about 2 cStk to about 500 cStk.

6. A composition according to claim 1 which comprises from about 5% to about 90%, by weight, polysiloxane fluid.

7. A composition according to claim 6 wherein the polysiloxane fluid is a polydimethylsiloxane fluid.

8. A composition according to claim 1 wherein the weight ratio between the silicone resin and the silicone gum is in the range from about 0.1:1 to about 9:1.

9. A composition according to claim 1 wherein the weight ratio between the polysiloxane fluid and the high molecular weight silicone gum is in the range from about 0.1:1 to about 20:1.

10. A composition according to claim 1 wherein the oral care active is selected the group consisting of teeth colour modifying substances, anti-tartar agents, anti-plaque agents, fluoride ion sources, anti-microbial agents and mixtures thereof.

11. A composition according to claim 10 wherein the oral care active is selected from the group consisting of peroxides, polyphosphates, xylitol, triclosan, stannous fluoride, soluble zinc salts, potassium nitrate and mixtures thereof.

12. A composition according to claim 1 which comprises from about 0.01% to about 20%, by weight, of an oral care active.

13. A composition according to claim 1 wherein the composition is a water in silicone emulsion and wherein the emulsion comprises from about 5% to about 95%, by weight, of the composition.

14. A composition according to claim 13 wherein the internal aqueous phase comprises rheology modifiers selected from the group consisting of cellulose polymers, xanthan gum, carbomers, inorganic clay polymers, polycarboxylates, EO/PO block copolymers (poloxamers), thickening silicas and mixtures thereof.

15. A composition according to claim 13 which comprises from about 0.001% to about 90%, by weight, of water.

16. A method of treating hard and soft tissue surfaces of a subject's oral cavity with a nonvolatile oral care composition comprising:
   i) from about 0.5% to about 60%, by weight, of a silicone resin;
   ii) from about 0.1% to about 30%, by weight of a silicone gum;
   iii) from about 0.1% to about 95%, by weight, of a non volatile polysiloxane fluid which has a viscosity from about 1 cStk to about 1000 cStk.

17. A method according to claim 16 wherein the nonvolatile oral care composition also comprises an oral care active selected from the group consisting of teeth color modifying substances, anti-tartar agents, anti-plaque agents, fluoride ion sources, anti-microbial agents, nutrients, antioxidants, H-2 antagonists, analgesics, anti-viral agents, mucosally absorbed pharmacological agents and mixtures thereof.

* * * * *